(12) United States Patent
Cushing et al.

(10) Patent No.: US 12,206,196 B2
(45) Date of Patent: Jan. 21, 2025

(54) RESPIRATORY EFFORT BELT CONNECTOR SYSTEM

(71) Applicants: Jay Cushing, Gainesville, FL (US); Jake Johnson, Ponte Vedra Beach, FL (US); John Saren, Gainesville, FL (US); James Schubert, Gainesville, FL (US)

(72) Inventors: Jay Cushing, Gainesville, FL (US); Jake Johnson, Ponte Vedra Beach, FL (US); John Saren, Gainesville, FL (US); James Schubert, Gainesville, FL (US)

(73) Assignee: Neurotronics, LLC, Alachua, FL (US)

(*) Notice: Subject to any disclaimer, the term of this patent is extended or adjusted under 35 U.S.C. 154(b) by 455 days.

(21) Appl. No.: 17/854,204

(22) Filed: Jun. 30, 2022

(65) Prior Publication Data
US 2024/0006795 A1      Jan. 4, 2024

(51) Int. Cl.
| | |
|---|---|
| A44B 11/00 | (2006.01) |
| A44B 11/25 | (2006.01) |
| H01R 13/428 | (2006.01) |
| H01R 35/04 | (2006.01) |
| A61B 5/00 | (2006.01) |
| A61B 5/113 | (2006.01) |

(52) U.S. Cl.
CPC .......... *H01R 13/428* (2013.01); *A44B 11/005* (2013.01); *A44B 11/2592* (2013.01); *H01R 35/04* (2013.01); *A61B 5/1135* (2013.01); *A61B 5/6831* (2013.01); *H01R 2201/12* (2013.01)

(58) Field of Classification Search
CPC .. H01R 13/428; H01R 35/04; H01R 2201/12; A44B 11/005; A61B 5/6831
See application file for complete search history.

(56) References Cited

U.S. PATENT DOCUMENTS

| | | | | |
|---|---|---|---|---|
| 6,011,699 | A * | 1/2000 | Murray | H04M 1/0216 379/433.05 |
| 7,214,067 | B2 * | 5/2007 | Zaderej | H01R 39/64 439/31 |
| 7,253,774 | B2 * | 8/2007 | Kasamatsu | H01Q 1/1235 343/702 |
| 7,438,570 | B2 * | 10/2008 | Mori | H01R 13/62933 439/157 |
| 7,448,891 | B2 * | 11/2008 | Ahn | H01R 35/04 361/755 |

(Continued)

*Primary Examiner* — Phuong Chi Thi Nguyen
(74) *Attorney, Agent, or Firm* — The Rapacke Law Group, P.A.; Andrew S. Rapacke

(57) ABSTRACT

A respiratory effort belt connector system and method for securing the belt to the user's body is provided. The respiratory effort belt connector system includes a belt coupled to the grip of a connector and a receptacle housing. The receptacle housing having a receptacle opening, a guide notch, a locking recess, and a locking lug located above the locking recess. The connector includes a barrel having an end configured to be inserted into the receptacle opening and a locking bar coupled to the barrel. The locking bar is configured to be aligned and inserted into the guide notch and then rotated into the locking recess where the locking bar/connector are retained by the locking lug of the receptacle. A connector neck couples the grip, which is configured to be accessible, to the barrel.

20 Claims, 11 Drawing Sheets

(56) References Cited

U.S. PATENT DOCUMENTS

| | | | |
|---|---|---|---|
| 7,469,451 B2* | 12/2008 | Hashizume | G06F 1/1683 |
| | | | 16/225 |
| 7,637,745 B1* | 12/2009 | Dai | H05K 1/147 |
| | | | 439/31 |
| 8,650,714 B2* | 2/2014 | Staude | E05D 11/0081 |
| | | | 439/31 |

* cited by examiner

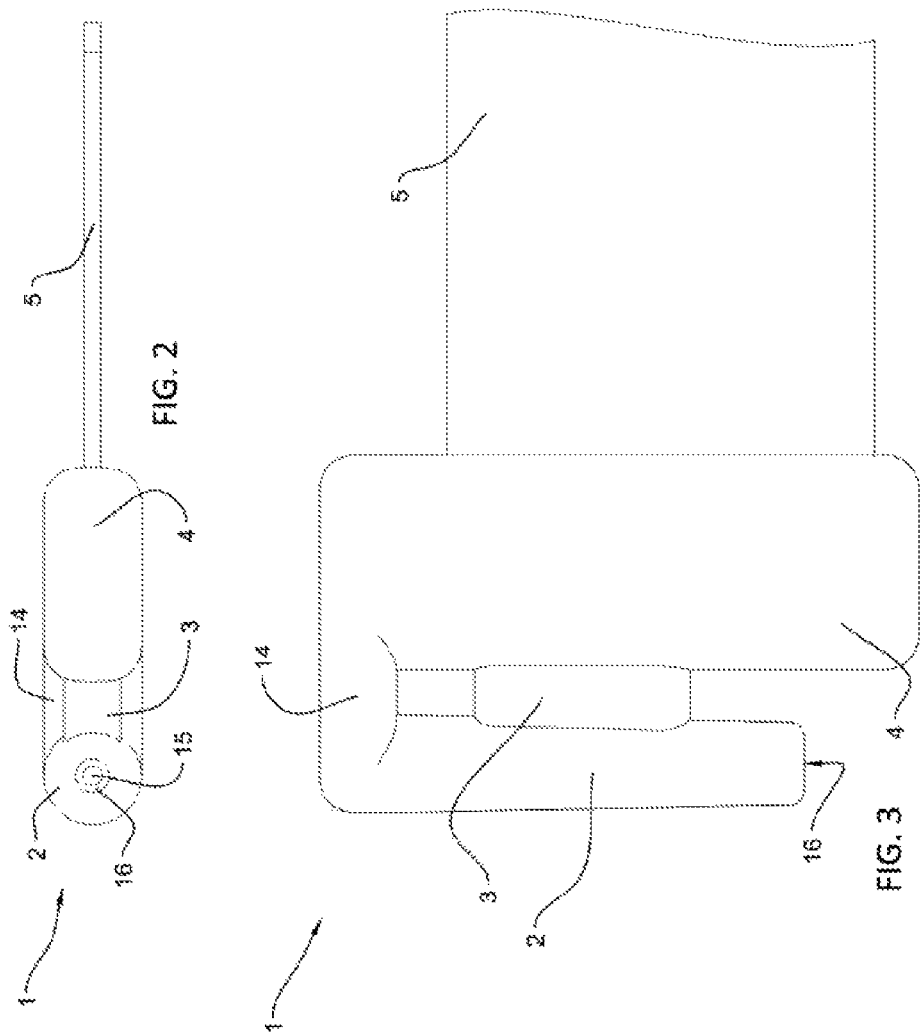

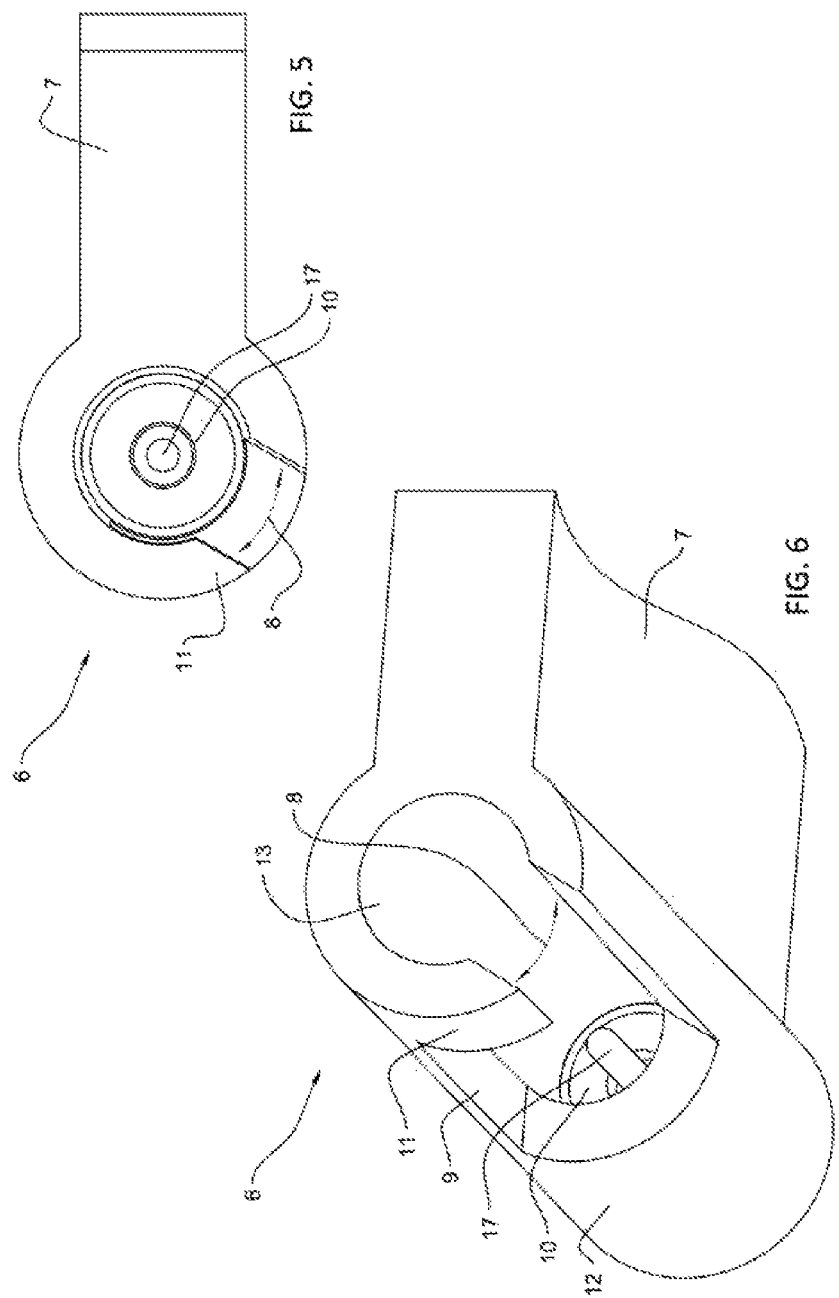

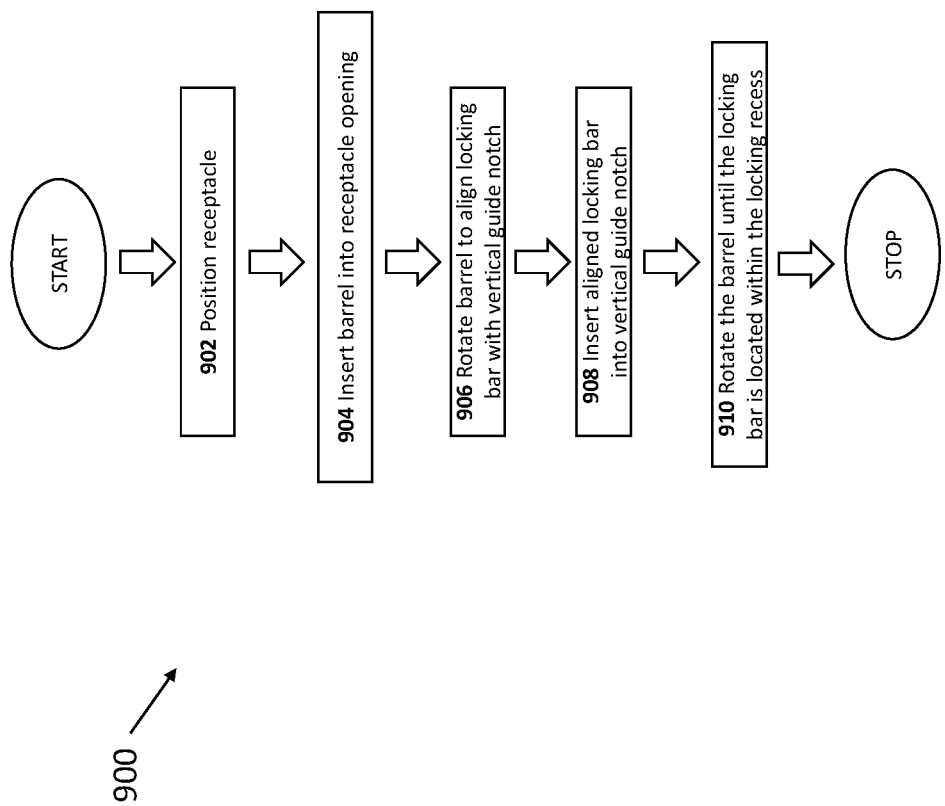

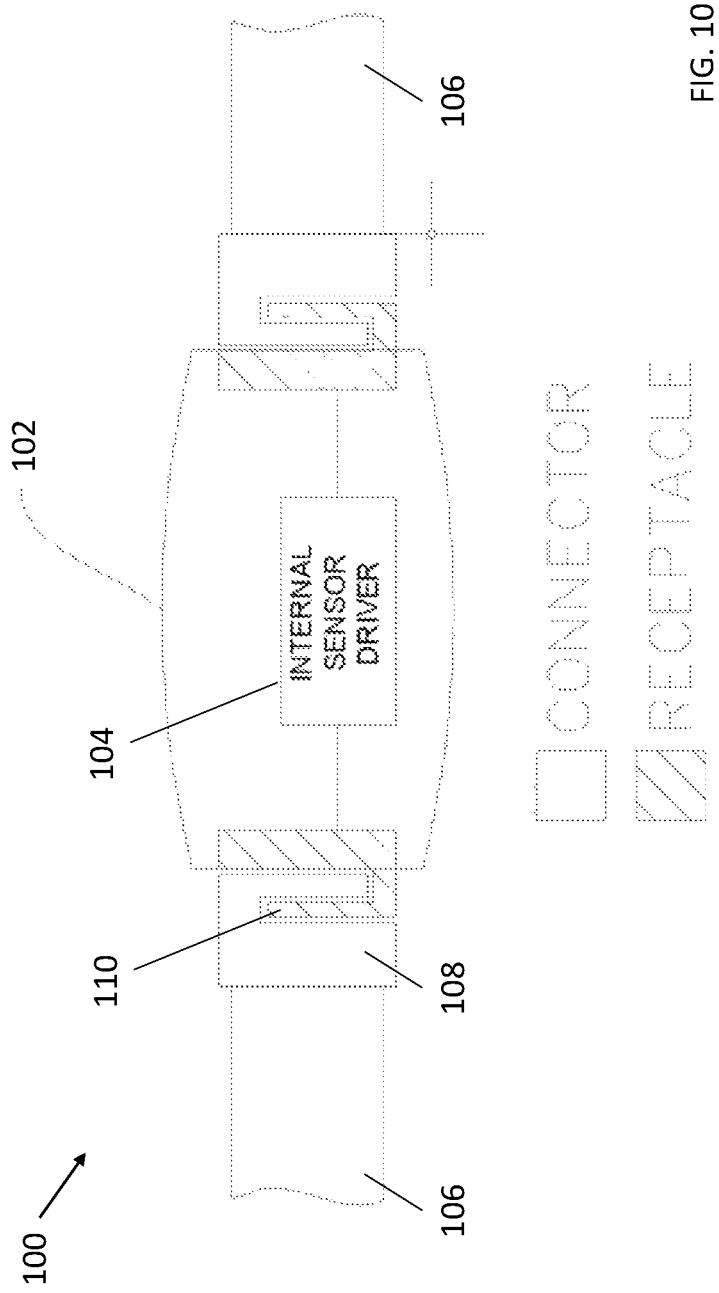

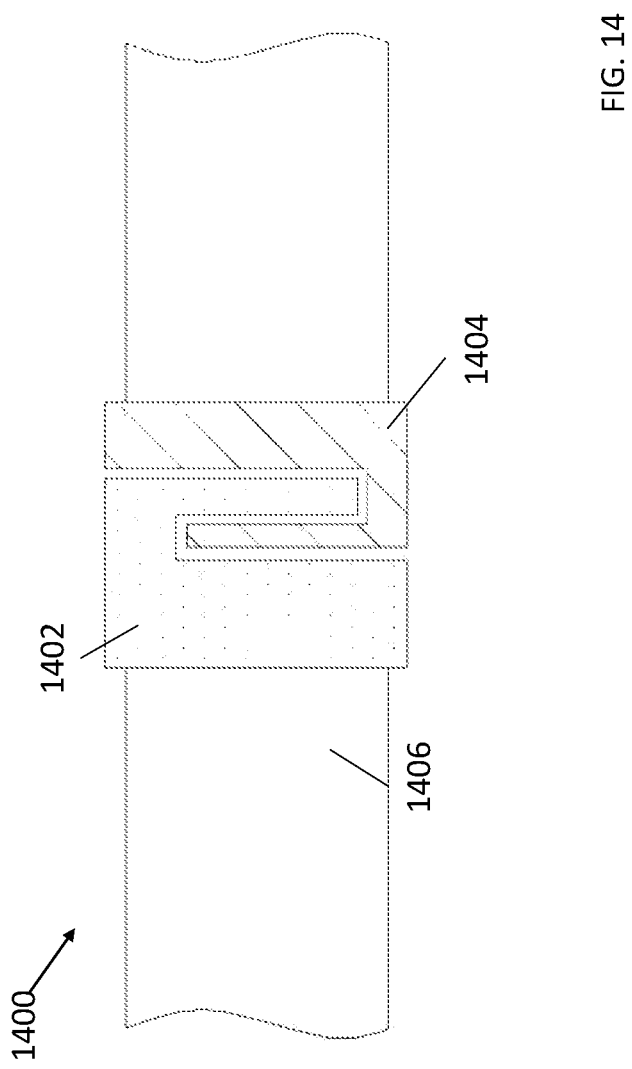

RESPIRATORY EFFORT BELT CONNECTOR SYSTEM

FIELD

The present disclosure relates to a respiratory effort sensor connector system, and more particularly to a mechanism for securing a respiratory effort belt to a user's chest or abdomen, with the capability of providing a reliable electrical connection if needed, and a method for securing the respiratory effort belt to a user.

BACKGROUND

Sleep is an integral aspect of our life and is needed to sustain our daily activity. The quality of our sleep has a massive influence on our health, our work performance, and our well-being. We spend almost one-third of our lifetime asleep and numerous research studies have shown a correlation between poor quality sleep and adverse health effects. However, most people who suffer from prevalent sleep disorders, like obstructive sleep apnea, are undiagnosed because these people are not aware of their symptoms while asleep and the limited availability and the high cost of polysomnography testing to identify sleep patterns and disorders.

Wearable respiratory sensors have been a required sensor for sleep studies for decades by clinicians and researchers in a wide range of applications. Monitoring respiratory effort can dramatically increase diagnosis accuracy and is essential when dealing with several diseases.

The proportion of sleep studies conducted in the home and other out-of-center environments has been steadily growing. However, usability issues with existing devices can lead to failure of a sleep study, leading to loss of time and resources for the patient and the sleep clinic. Many of the connection systems used with these existing wearable respiratory sensors have design features that present usability concerns for sleep studies, especially when the sleep study is to be performed at the patient's home without the aid of a clinician. Some of these existing connection systems use a clamp connector method with a frame, prong, and bar that slips into the notches of a belt strap for tightening or loosening. Others require the user to use a button snap connector. If a user has dexterity or strength issues, this may be a difficult task. Many of these existing connection systems also require the user to make electrical connections between sensors and the device and/or belt. This requires the manipulation of small wire leads and mating connectors, which in some instances are touchproof 1 mm, 1.5 mm, or small keyhole connections, when connecting the belt to the sensor(s) and monitoring device. If a user has dexterity issues, this may be a difficult task. Therefore, usability issues, especially for non-clinical users, are an increasingly important area for improvement.

There are also inherent problems with the use of small wire leads in an application such as this. The wires can get tangled with themselves, other sensors, or the patient, causing discomfort or accidental disconnection. Leads require the user to connect them to the correct receptacles and to ensure the connector is fully mated. Further, respiratory effort is a required parameter for sleep studies and existing connection systems can be accidently disconnected by that respiratory effort or the movement of the patient during the sleep study. If a sensor becomes disconnected, particularly at night during a home sleep study where a clinician is not available to intervene, the value of the sleep study is compromised.

For at least the foregoing reasons, there is a need for a reliable, easy to use respiratory effort belt connection system that can be used to maintain a connection to a sleep monitor device used in the analysis of different sleep parameters over time, in both home and clinical environments. In some embodiments, the proposed respiratory effort belt connection system allows users to monitor, and healthcare professionals to evaluate, diagnose, and treat patients of sleep studies in a more time efficient and cost-effective manner.

SUMMARY

In various embodiments, a respiratory effort belt connector includes a receptacle having a receptacle housing. The receptacle housing having a receptacle opening formed by a longitudinal cavity in the top portion of the receptacle housing, a guide notch formed by a vertical cavity in the side of the top the receptacle housing, and a locking recess formed by a rectangular cavity in the upper side portion of the receptacle housing. The longitudinal cavity, vertical cavity, and rectangular cavity are fluidly coupled. The receptacle housing also includes a locking lug located above the locking recess, formed by a portion of the side of the top of the receptacle housing without the guide notch. The respiratory effort belt connector has a barrel with an end configured to be inserted into the receptacle opening and a locking bar coupled to the barrel. The locking bar is configured to be aligned and inserted into the guide notch, rotated into the locking recess, and retain by the locking lug of the receptacle. The connector also has an accessible grip connected to the barrel by a connector neck.

In various embodiments, the grip of the respiratory effort belt connector is coupled to an end of the locking bar opposite that of the barrel and has a shape of a rectangular prism with rounded corners.

In various embodiments, the connector neck of the respiratory effort belt connector extends from the top section of the grip to the top portion of the barrel and has an internal cavity to allow an electrical conductor to pass between the grip and the barrel.

In various embodiments, the receptacle housing of the respiratory effort belt connector comprises another locking recess and another locking lug, and the connector comprises another locking bar coupled to the barrel.

In various embodiments, the locking recess adjacent to the guide notch of the respiratory effort belt receptacle is configured to be located nearer the user's chest or abdomen when the connector and the receptacle are coupled together.

In various embodiments, the barrel of the connector of the respiratory effort belt connector has a tapered cylindrical shape that substantially matches the shape of a central tapered cylindrical cavity formed in the receptacle housing, below the receptacle opening.

In various embodiments, the locking bar of the respiratory effort belt connector is located about midway along the length of the barrel and perpendicular to the central axis of the barrel.

In some embodiments, the respiratory effort belt further includes a connector electrical contact located within a touchproof recess formed by a cavity in the bottom of the barrel and a receptacle electrical contact located within a touchproof recess or connector well formed by a cavity in the base of the receptacle housing. The connector electrical contact and the receptacle electrical contact are rotary type electrical connectors.

In various embodiments, the width of the locking recess is between about 30 degrees and about 60 degrees.

In various embodiments, the width of the guide notch is about ⅓ the width of the receptacle housing.

In various embodiments, the aligned and inserted locking bar is configured to be rotated through an angle of about 60 degrees from the vertical guide notch into the locking recess.

In various embodiments, a method for securing a respiratory effort belt to a user is provided. This can include inserting the end of a barrel of a connector into a receptacle opening formed by a longitudinal cavity in the top portion of a receptacle housing of a receptable; rotating the barrel of the connector, with respect to the receptacle housing, until the bottom of a locking bar coupled to the barrel is substantially aligned with a vertical guide notch formed by a vertical cavity in the side of the top of the receptacle housing; inserting the aligned locking bar into the guide notch until the body of the locking bar is fully seated within the guide notch and adjacent to a locking recess formed by a cavity within the upper portion of the body of the receptacle housing; and rotating the barrel of the connector, with respect to the receptacle housing, until the locking bar is substantially located within the locking recess; wherein the locking bar is retained by a locking lug located above the locking recess, formed by a portion of the side of the top of the receptacle housing without the guide notch.

In various embodiments, the barrel of the connector utilized in the method has a tapered cylindrical shape that substantially matches the shape of a central tapered cylindrical cavity formed in the receptacle housing below the receptacle opening.

In various embodiments, the locking bar utilized in the method is located about midway along the length of the barrel and perpendicular to the central axis of the barrel.

In some embodiments, the method can include positioning the receptacle so that that the locking recess adjacent to the guide notch is nearer the user's chest or abdomen.

Additional features and advantages of the embodiments disclosed herein will be set forth in the detailed description that follows, and in part will be clear to those skilled in the art from that description or recognized by practicing the embodiments described herein, including the detailed description which follows, the claims, as well as the appended drawings.

Both the foregoing general description and the following detailed description present embodiments intended to provide an overview or framework for understanding the nature and character of the embodiments disclosed herein. The accompanying drawings are included to provide further understanding and are incorporated into and constitute a part of this specification. The drawings illustrate various embodiments of the disclosure, and together with the description explain the principles and operations thereof.

BRIEF DESCRIPTION OF THE DRAWINGS

The features and advantages of the present disclosure will be more fully described in, or rendered obvious by, the following detailed description of the preferred embodiments, which are to be considered together with the accompanying drawings, wherein like numbers refer to like parts and further, wherein:

FIG. 2 is a bottom view of a connector of the respiratory effort connector system in FIG. 1, in accordance with some embodiments described herein;

FIG. 3 is a front view of the connector of the respiratory effort connector system in FIG. 1, in accordance with some embodiments described herein;

FIG. 5 is a top view of a receptacle of the respiratory effort connector system in FIG. 1, in accordance with some embodiments described herein;

FIG. 6 is an upper perspective view of the receptacle of the respiratory effort connector system in FIG. 1, in accordance with some embodiments described herein;

FIG. 9 is a flow diagram illustrating a process of securing a respiratory effort belt connector, in accordance with some embodiments described herein.

FIG. 10 is a front perspective view of a respiratory effort connector system coupled with a home sleep apnea test (HSAT) device with integrated sensor driver;

FIG. 14 is a front perspective view of an inert respiratory effort connector system.

DETAILED DESCRIPTION

Figure 1:
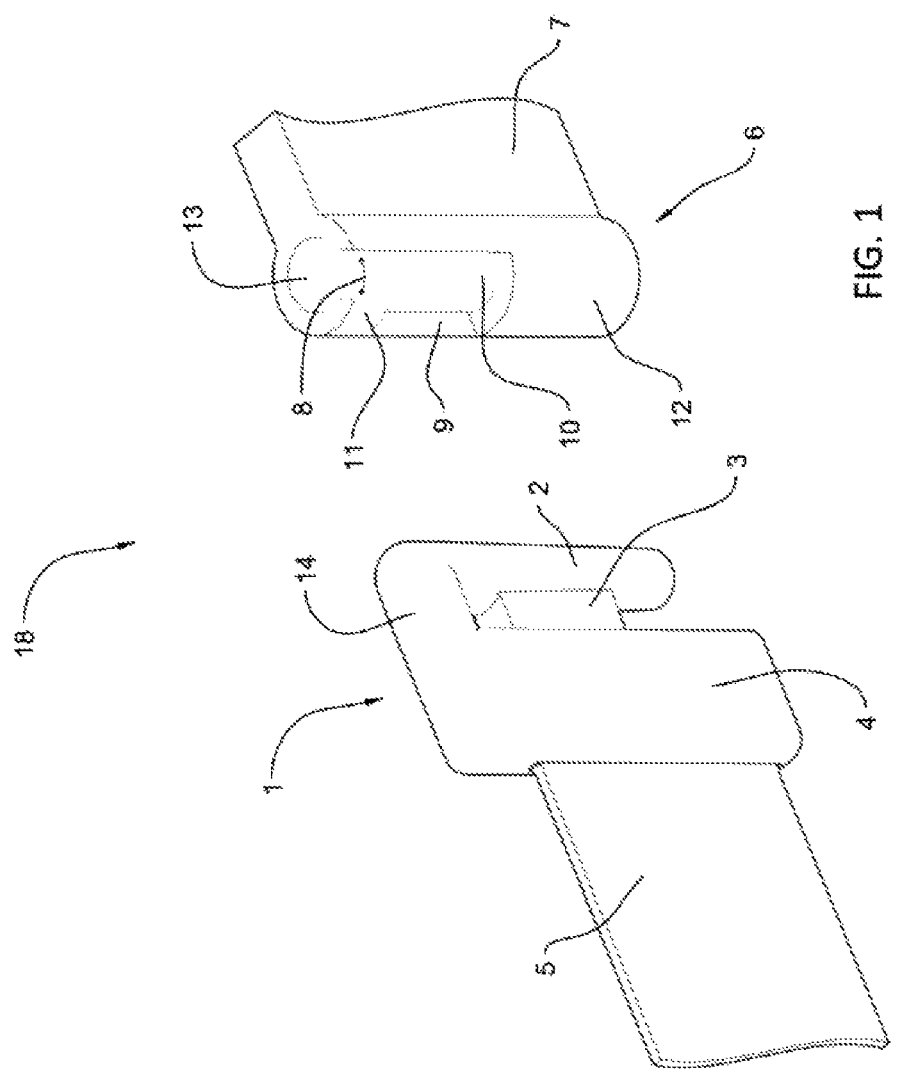
FIG. 1 is an upper perspective view of a respiratory effort belt connection system, in accordance with some embodiments described herein.

Reference will now be made in detail to the present preferred embodiment(s), examples of which is/are illustrated in the accompanying drawings. Whenever possible, the same reference numerals will be used throughout the drawings to refer to the same or like parts.

In various embodiments, as shown in FIGS. 1-9, a respiratory belt connector system, and more particularly to a mechanism for securing a respiratory effort belt to user's chest, abdomen, or other body location, with the capability of providing a reliable electrical connection if needed, and a method for securing a respiratory effort belt to a user is provided.

The upper perspective view of FIG. 1 provides an illustrative example of a respiratory effort belt connector system 18. The respiratory effort connector system 18 is designed to have a low profile and be comfortable to wear and easy to use, even by those users with limited dexterity, at home. In some embodiments, the respiratory effort connector system 18 includes two primary parts, a connector 1, attached to a belt 5, and a receptacle 6, attached to a sleep monitor device 7, or vice versa. In some embodiments, the connector is not connected to a device, while in other embodiments it can be connected to other devices. Connector 1 mates with and locks into the receptacle 6, which is attached to the sleep monitor device 7. As shown in FIG. 1, in some embodiments, the connector 1 and receptacle 6 are not coupled together or mated.

In some embodiments, the connector 1 terminates the end of a belt 5 and the sleep monitor device 7, coupled to the receptacle 6, terminates the other end of the belt 5. Alternatively, the receptacle 6 can terminate the end of the belt 5 and the sleep monitor device 7, coupled to the connector 1, can terminate the belt 5 (not shown). In some embodiments, the relative positions of the connector 1 and receptacle 6 may be flipped to facilitate the use of the respiratory effort connection system 18 by left and right-handed users. In some embodiments, the respiratory effort connector system 18 may be implement as two connectors 1 coupled to the belt 5 that mate with two receptacles 6 coupled to the sleep monitor device 7.

In some embodiments, as shown in FIG. 1 the respiratory effort belt of the respiratory effort connection system 18 comprises the receptacle 6 having a receptacle housing 12. The receptacle housing 12 comprises a receptacle opening 13 formed by a longitudinal cavity in the top portion of the receptacle housing 12. The receptacle housing 12 also comprises a guide notch 8 formed by a vertical cavity in the side of the top the receptacle housing 12. The receptacle housing 12 also comprises a locking recess 9 formed by a rectangular cavity in the upper side portion of the receptacle housing 12. The longitudinal cavity, vertical cavity, and rectangular cavity are fluidly coupled. The receptacle housing 12 further comprises a locking lug 11 located above the locking recess 9, which is formed by a portion of the side of the top of the receptacle housing 12 without the guide notch 8.

In various embodiments, as shown in FIG. 1, the respiratory effort belt of the respiratory effort connection system 18 also comprises the connector 1. The connector 1 comprises a barrel 2 having an end configured to be inserted into the receptacle opening 13 of the receptacle housing 12. The connector 1 also comprises a locking bar 3 coupled to the barrel 2, which is configured to be aligned and inserted into the guide notch 8, then rotated into the locking recess 9 where the locking bar 3 is retain by the locking lug 11 of the receptacle 6. The connector 1 further comprises a connector neck 14 coupling the top of a grip 4 to the top of the barrel 2.

In some embodiments, the connector 1 is comprised of a molded polymer structure. In some embodiments, the connector 1 includes a cylindrical barrel 2, which may be tapered, attached to one end of a locking bar 3. The locking bar 3 may be attached to a side of the barrel 2, such that the locking bar 3 is located about midway along the length of the barrel 2 and perpendicular to the central axis of the barrel 2. In various embodiments, as shown in FIG. 1, the locking bar 3 has a generally rectangular shape with sharp corners. However, other three-dimensional shapes that securely engage are contemplated. A grip 4 may be attached to an end of the locking bar 3 opposite that of the barrel 2. In some embodiments, the three-dimensional shape of the grip 4 may be that of a rectangular prism and include a connector neck 14 extending from the top portion of the grip 4 to the top portion of the barrel 2. Locking bar 3 can have rounded corners in some embodiments. In various embodiments, as shown in FIG. 1, the grip 4 has a generally rectangular shape with rounded corners and the connector neck 14 has a generally cylindrical shape. However, other three-dimensional shapes that are easy to grip are contemplated.

In some embodiments, the grip 4, connector neck 14, barrel 2, receptacle housing 12, and body of the sleep monitoring device 7, or other device, are thermoplastic materials. These thermoplastic materials include polycarbonate, polypropylene, polyethylene, and the like. Custom polymers and/or metal alloys and plating may be used for sliding surfaces and precision components the locking bar 3, guide notch 8, locking recess 9, and locking lug 11. In some embodiments the belt connector can be preferably made from any of various suitable non-conducting plastic materials, such as but not limited to polyamide (nylon), PC/ABS, polyethylene, polypropylene, or more preferably ABS (acrylonitrile butadiene styrene).

In some embodiments, the belt 5 comprises a polyvinylidene fluoride (PVDF) or piezo crystal technology sensing element responsive to strain. In some embodiments, the belt 5 comprises an inductance-type sensing element (e.g. for Respiratory Inductance Plethysmography (RIP)), where a wire or other electrical conductor is interwoven or laminated into the belt 5, typically in a sinusoidal or zig-zag fashion to allow for longitudinal elasticity. In some embodiments, the belt 5 comprises a capacitance-type sensing element having an elastically deformable sheet-like dielectric, and a sheet-like conductor arranged within the body of the belt 5 configured to measure the extension and contraction of the user's chest or abdomen.

In some embodiments, the belt 5 is a reusable belt. In various embodiments, the respiratory effort connector system 18 is a semi-disposable solution and the belt 5 is a disposable belt. The size of the belt 5 can be adjustable or come in different sizes to accommodate infants, toddlers, children, and adults of various sizes.

While the respiratory effort connector system 18 may be implemented without electrical contacts for the belt 5 in some embodiments the respiratory effort connector system 18 may also include electrical contacts. In some embodiments, the connector neck 14 may contain an internal cavity to allow electrical conductors for the belt 5 to pass between the grip 4 and the barrel 2. In other embodiments, that do not require an electrical connection for the belt 5 the connector neck 14 may not include an internal cavity.

FIG. 2 shows a bottom view of the connector 1 of the respiratory effort connector system 18. While the respiratory effort connector system 18 may be implemented without electrical contacts for the belt 5 in some embodiments the connection system may also include electrical contacts. When an electrical connection is desired in addition to a mechanical connection, the barrel 2, may house a connector electrical contact 15. To protect the connector electrical contact 15, the electrical contact 15 may be located within a cavity within the body of the connector 1. This configuration also prevents the user from accidentally touching the electrical contact 15. In various embodiments, as shown in FIG. 2 the connector electrical contact 15 is located within a touchproof recess or electrical contact recess 16, formed by a cavity in the bottom of the tapered cylindrical barrel 2 opposite the connector neck 14. FIG. 2 also shows in more detail the bottom of the locking bar 3, the grip 4, the belt 5, and the connector neck 14.

FIG. 3 shows a front view of the connector 1 of the respiratory effort connector system 18 illustrating in more detail the size and shapes of tapered cylindrical barrel 2 and locking bar 3 and their respective locations. FIG. 3 also shows more detail of the front of the tapered cylindrical barrel 2, the grip 4, the belt 5, the connector neck 14, and the position of the electrical contact recess 16 within the bottom of the tapered cylindrical barrel 2.

Figure 4:
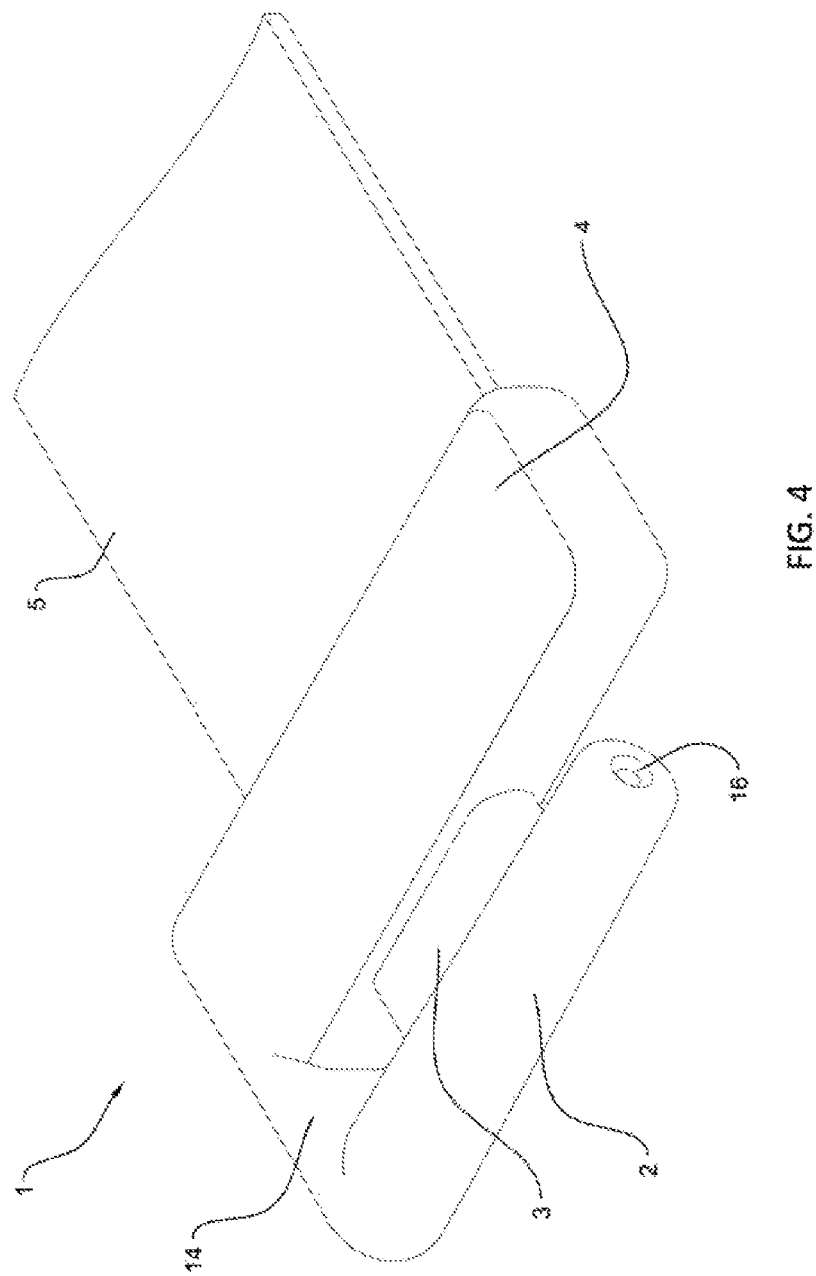
FIG. 4 is an upper front perspective view of the connector of the respiratory effort connector system in FIG. 1, in accordance with some embodiments described herein.

FIG. 4 shows an upper perspective view of the connector 1 of the respiratory effort connector system 18 illustrating in more detail the size and shape of the tapered cylindrical barrel 2 and locking bar 3, and their locations with respect to the connector neck 14 and grip 4. FIG. 4 also shows in more detail the position of the electrical contact recess 16 within the bottom of the tapered cylindrical barrel 2 and the coupling of the belt 5 to the grip 4.

FIG. 5 shows a top view of the receptacle 6 of the respiratory effort connector system 18, illustrating in more detail the receptacle electrical contact 17 within the connector well 10 of the receptacle housing 12, and the guide notch 8 formed in the side of the top of the receptacle housing 12. The portion of the top of the receptacle housing 12 without the guide notch 8 forms the locking lug 11.

While the respiratory effort connector system 18 may be implemented without electrical contacts for the belt 5 in some embodiments the respiratory effort connection system 18 may also include both electrical and mechanical connections. When an electrical connection is desired in addition to a mechanical connection the receptacle housing 12 may house a receptacle electrical contact 17. In some embodiments, the receptacle electrical contact 17 may protrude up from the bottom of the connector well 10 into the central cavity of the receptacle housing 12. To protect the receptacle electrical contact 17, the electrical contact 17 may be located within a cavity or recess within the body of the receptacle 6. This configuration also prevents the user from accidentally touching the electrical contact 17. In various embodiments, as shown in FIG. 5 the receptacle electrical contact 17 is located within a touchproof recess or connector well 10 formed by a cavity in the base of the receptacle housing 12.

In some embodiments, the receptacle electrical contact 17 is a pin-shaped plug-in jack that is similar or analogous to a 2.5 mm (micro) or a 3.5 mm (mini) standard jack used on music headphones. The length of the receptacle electrical contact 17 is between about 7 mm and about 8 mm. In certain embodiments, the length of the receptacle electrical contact 17 is about 15 mm. Various embodiments include the pin-shaped plug-in jack having a ground connection and either a single (two pole), multiple 2 (3 pole) or 3 (4 pole), electrical signal connections.

In some embodiments, the materials used for the various components of the respiratory effort connector system 18 include stainless steel, cobalt-chromium alloys, titanium alloys, thermoplastic, epoxy resin, nickel alloys, copper alloys, and the like. Electrical contacts like the connector electrical contact 15 and the receptacle electrical contact 17 are made from metals or a metal alloy with high electrical conductivity. In various embodiments, the metal surfaces of the connector electrical contact 15 and the receptacle electrical contact 17 can be alloys of aluminum, copper, gold, platinum, palladium, beryllium, tin, and nickel. For example, the connector electrical contact 15 and the receptacle electrical contact 17 may be gold plated.

FIG. 5 also shows in more detail the top of the locking lug 11, the guide notch or notch cutout 8, and the mating device.

FIG. 6 shows an upper perspective view of the receptacle 6 of the respiratory effort connector system 18, illustrating in more detail the location of the receptacle electrical contact 17 within the connector well 10 and the locking lug 11. In various embodiments, as shown in FIG. 6, there is a locking recess 9 formed by a cavity in the upper portion of the receptacle housing 12 which is fluidly coupled to the lower portion of the guide notch 8. The locking lug 11 is located at the top of the locking recess 9. The locking lug 11 retains the locking bar 3 of the connector 1 within the locking recess 9 after the locking bar 3 has been rotated into the locked position during connector mating. The side walls of the locking recess 9 form solid stops for the locking bar 3 of the connector 1 and provide tactile feedback to the user during the locking and unlocking process.

In some embodiments, the orientation of the locking recess 9 is facing the user's abdomen or chest (diaphragm). That is, the respiratory effort connector system 18 is designed to prevent accidental releases because the force exerted by breathing increases the retention of the locking bar 3 within the locking recess 9. As such, the locking mechanism is designed so that when the belt 5 is connected and worn around the user, typically around the chest or abdomen, the natural lay of the belt 5 keeps the connection in the locked position. Accidental release is prevented by belt tension preventing the connector from rotating out of the locking recess. In some embodiments, the receptacle 6 is comprised of a molded polymer structure.

In some embodiments, the width of the guide notch 8 is between about 30 degrees and about 60 degrees or between about 5 mm and 10 mm, although other angles and sizes are contemplated. In various embodiments, the width of the guide notch 8 is about ⅓ of the width of the receptacle housing 12. For example, the width of the guide notch 8 is about 45 degrees or about 7 mm. The guide notch 8 may have straight or tampered edges.

In some embodiments, the width of the locking recess 9 is between about 30 degrees and about 60 degrees or between about 5 mm and 10 mm, although other angles and sizes are contemplated. In various embodiments, the width of the locking recess 9 is about ⅓ of the width of the receptacle housing 12. For example, the width of the locking recess 9 is about 45 degrees or about 7 mm. The guide notch 8 may have straight or tampered edges. In certain embodiments, the width of the notch 8 and the locking recess 9 are substantially the same. Therefore, the locking bar 3 rotates through angle of between about 30 degrees and 60 degrees from the vertical guide notch 8 into the locking recess 9. 60 degrees of rotation may be required to fully lock or unlock the connector. In some embodiments, the locking bar 3 rotates through an angle of about 45 degrees from the vertical guide notch 8 into the locking recess 9. Consequently, the user must displace the locking bar 3 by an equivalent angle and then vertically displace the locking bar 3 out of the receptacle opening 13 to accidently unlock the respiratory effort connector system 18 during sleep. In various embodiments, the degree of rotational movement may be configured by changing the width of the locking bar 3 and guide notch 8, with respect to the width of the locking recess 9.

Figure 7:
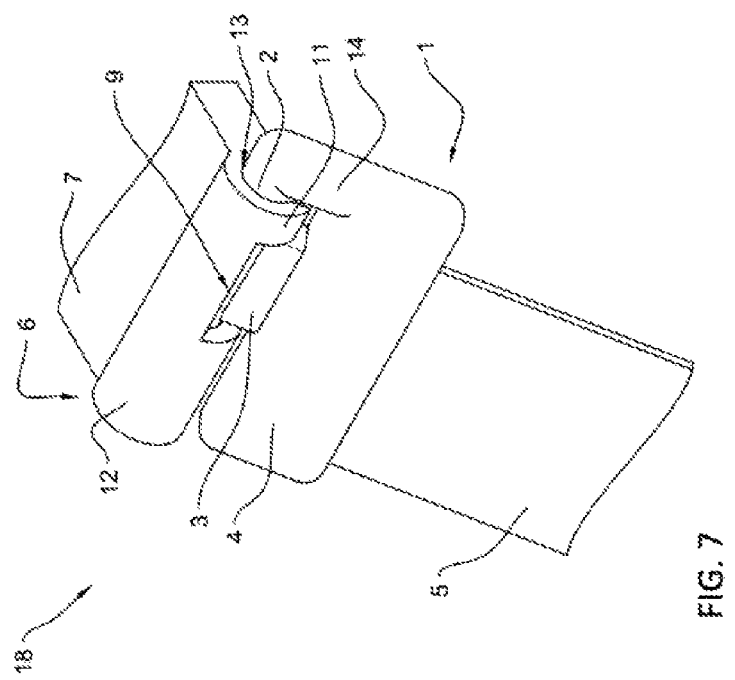
FIG. 7 is a front perspective view of the respiratory effort connection system in FIG. 1, having the connector mated to the receptacle and a locking bar in the unlocked position, in accordance with some embodiments described herein.

FIG. 7 shows a front perspective view of the respiratory effort connector system 18 of FIG. 1 with the connector 1 mated to the receptacle 6 and illustrating in more detail the locking bar 3 in the unlocked position. In some embodiments, the belt 5 is mated to the device 7 by inserting the end of the barrel 2 of the connector 1 into the receptacle opening 13 formed in the top of the receptacle housing 12 of the receptacle 6. Rotating the barrel 2 of the connector 1 until the bottom of the locking bar 3 coupled to the barrel 2 is substantially aligned with the guide notch 8 formed in the side of the side of the top of the receptacle housing 12. Then, pressing the barrel 2 completely into the connector well 10 until the locking bar 3 is fully seated within the guide notch 8. Although the locking bar 3 is fully seated within the guide notch 8 the body of the locking bar 3 is still outside the locking recess 9 in this position. Because the body of the locking bar 3 is outside the locking recess 9, and therefore not engaged by the locking lug 11, the barrel 2 of the connector 1 may freely move within the receptacle housing 12. However, provided the locking bar 3 remains fully seated within the guide notch 8 the respiratory effort connector system 18 is still able to form a stable electrical connection between the connector 1 and the receptacle 6

Figure 8:
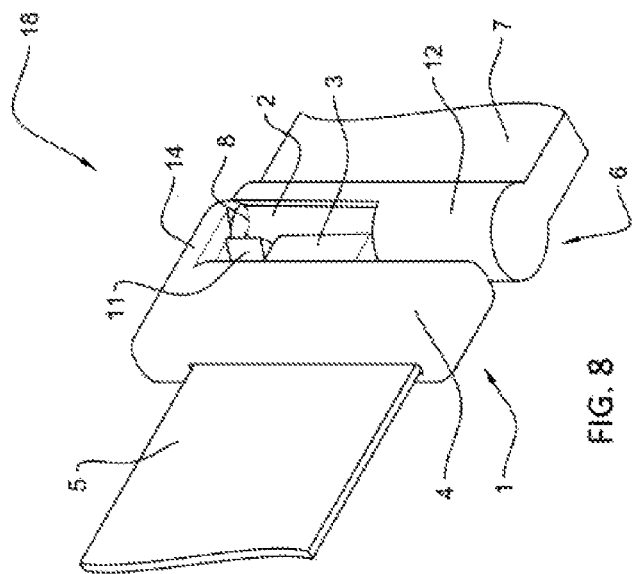
FIG. 8 is a rear perspective view of the respiratory connection system in FIG. 1, having the connector mated to the receptacle and the locking bar in the locked position, in accordance with some embodiments described herein.

FIG. 8 shows a rear perspective view of the respiratory effort connector system 18 of FIG. 1 with the connector 1 mated to the receptacle 6 and illustrating in more detail the locking bar 3 in the locked position. In some embodiments, the belt 5 is mated to the sleep monitor device 7 or other device by lining up the locking bar 3 on the connector 1 with the guide notch 8 on the receptacle 6. Then, sliding the barrel 2 completely into the connector well 10, and rotating the connector 1 with respect to the receptacle 6 until the locking bar 3 sits within the locking recess 9. In the locked position, the locking bar 3 is fully engaged within the locking recess 9 of the receptacle 6 by the locking lug 11, preventing removal of the belt 5, while still allowing a degree of rotation movement. When fully seated, the respiratory effort connector system 18 forms a stable mechanical connection between the connector 1 and the receptacle 6, while still allowing a degree of rotational movement. This configuration provides a respiratory effort connector system 18 that is easily mated and unmated, while also being difficult to accidentally unmate during a sleep study. This configuration also provides a respiratory effort connector system 18 that is more comfortable to wear during sleep because respiratory effort connector system 18 conforms to user's body and adapts to movement of the user during the sleep study. Further, the large area of the grip 4 of the connector 1 and receptacle 6 makes manipulating connector easy for those users with reduced dexterity. Also illustrated in FIG. 8 is a more detailed rear perspective view of the receptacle housing 12 and the connector neck 14.

In various embodiments, the respiratory effort connector system 18 can also form a stable electrical connection between the belt 5 and sleep monitor device 7, while still allowing a degree of rotational movement because the connector electrical contact 15 and receptacle electrical contact 17 are rotary type electrical connectors. In some embodiments, the electrical contact is a round pin design that allows rotation.

Conversely, to unmate the belt 5 from the sleep monitor device 7, the connector 1 is rotated with respect to the receptacle 6 until the locking bar 3 sits outside the locking recess 9 and fully within the guide notch 8 on the receptacle 6. Then, sliding the barrel 2 out of the tapered recess until the bottom of the barrel 2 is clear of the receptacle housing 12.

Example Processes

To enable the reader to obtain a clear understanding of the technological concepts described herein, the following processes describe specific steps performed in a specific order. However, one or more of the steps of a particular process may be rearranged and/or omitted while remaining within the contemplated scope of the technology disclosed herein. One or more processes and/or steps thereof, may be combined, recombined, rearranged, omitted, or executed in parallel to create different process flows that are within the contemplated scope of the technology disclosed herein. While the processes below may omit or briefly summarize some of the details of the technologies disclosed herein for clarity, the details described in the paragraphs above may be combined with the process steps described below to get a more complete and comprehensive understanding of these processes and the technologies disclosed herein.

FIG. 9 is an example flow diagram of a process for securing a respiratory effort belt to a patient by either the patient themselves or a medical practitioner. In some embodiments, the process 900 begins with step 902, in which a medical practitioner or the patient positions a receptacle 6 so that a locking recess 9 adjacent to a guide notch 8 in the receptacle housing 12 is nearer to the patient's chest or abdomen than the adjacent guide notch 8. In step 904, the patient or medical practitioner, hereinafter user, inserts the end of a barrel 2 of a connector 1 into a receptacle opening 13 formed by a longitudinal cavity in the top portion of a receptacle housing 12. Next in step 906, the user rotates the barrel 2 of the connector 1 with respect to the receptacle housing 12 until the bottom of a locking bar 3 coupled to the barrel 2 is aligned with a vertical guide notch 8 formed by a vertical cavity in the side of the top of the receptacle housing 12. Next in step 908, the user inserts the aligned locking bar 3 into the guide notch 8 until the body of the locking bar 3 is fully seated within the guide notch 8 and adjacent to a locking recess 9 formed by a cavity within the upper portion of the body of the receptacle housing 12. Next in step 910, the user rotates the barrel 2 with respect to the receptacle housing 12 until the locking bar 3 is located within the locking recess 9, wherein the locking bar is retained by a locking lug 11 located above the locking recess 9 formed by a portion of the side of the top of the receptacle housing 12 without the guide notch 8. This completes the process 900 for securing the respiratory effort belt to the patient's chest or abdomen. One end of the belt may be attached to a device before the belt is to be secured to a patient in some embodiments.

The connectors and connection systems and methods described herein can be used in conjunction with a variety of sensors and belts in various embodiments. These can include Respiratory Inductance Plethysmography (RIP) Effort Belts, Polyvinylidene fluoride (PVDF) belts, Piezo Crystal Belts, Device Support Belts (i.e. belts with no sensing mechanisms attached), and others.

Furthermore, these connectors can be used in connection with a sleep amplifier, which is a device that acquires physiological signals from a patient during a sleep study. These signals are sampled from multiple sources such as patient-worn sensors, electrodes, external devices, and others. Some versions of these connectors can be implemented with respiratory effort belts that connect directly to a home sleep apnea test (HSAT) device. Other versions can interface with other types of devices, where a direct connection to a belt is not possible.

FIG. 10 is a front perspective view 100 of a respiratory effort connector system coupled with an HSAT device 102 with integrated sensor driver 104. As shown in the example embodiment, a respiratory effort belt 106 can have a connector 108 on each belt end. These connectors 108 can be coupled or mated with receptacles 110 on the HSAT device 102. The HSAT device 102 can contain circuitry to drive the sensor 104 internally. This is an improvement over existing systems where an HSAT device is mounted on a separate belt and the respiratory effort belt requires an additional sensor driver device.

In various embodiments, connector 1 can be made from any of various suitable non-conducting plastic materials, such as but not limited to polyamide (nylon), PC/ABS, polyethylene, polypropylene, or more preferably ABS (acrylonitrile butadiene styrene). The connector 1 can be made through casting or more preferably through injection molding. The connector 1 can be constructed of two mating halves that are attached to one another through adhesive, chemical bonding or more preferably ultrasonic welding. In some embodiments where ingress protection is needed an ingress prevention seal is applied in the connector neck 14. This seal can be made from but not limited to materials such as silicone or epoxy resin.

Belt 5 can be mechanically coupled to the connector 1 in some embodiments through direct over molding or more preferably by mechanically pinning the connector 1 to the belt material during assembly.

Connector electrical contact 15 can be coupled or attached mechanically to connector 1 in some embodiments by means of insert molding or more preferably by press fit into an internal cavity of connector 1. The connector electrical contact 15 is attached electrically to the belt 5 through a soldered or preferably a crimped connection. The contact can be made from but not limited to alloys of copper, beryllium, tin, gold, nickel.

In various embodiments, receptacle 6 is s preferably made from any of various suitable non-conducting plastic materials, such as but not limited to polyamide (nylon), PC/ABS, polyethylene, polypropylene, or more preferably ABS (acrylonitrile butadiene styrene). The receptacle 6 can be made through casting or more preferably through injection molding. The receptable 6 can be constructed of a single piece mechanically attached to the connected device 7, preferably molded directly into the device 7.

Receptacle electrical contact 17 can be coupled or attached mechanically to receptable 6 in some embodiments by means of insert molding, adhesive, or more preferably by press fit into an internal cavity of receptable 6. Receptacle electrical contact 17 can be coupled or attached electrically to the device 7 through a soldered, crimped or preferably a direct socketed connection. The contact 17 is made from but not limited to alloys of copper, beryllium, tin, gold, nickel.

In some embodiments where ingress protection is needed, an ingress prevention seal can be employed or used in the connector well 10. This seal can be made from but not limited to materials such as silicone or EPDM rubber.

Figure 11:
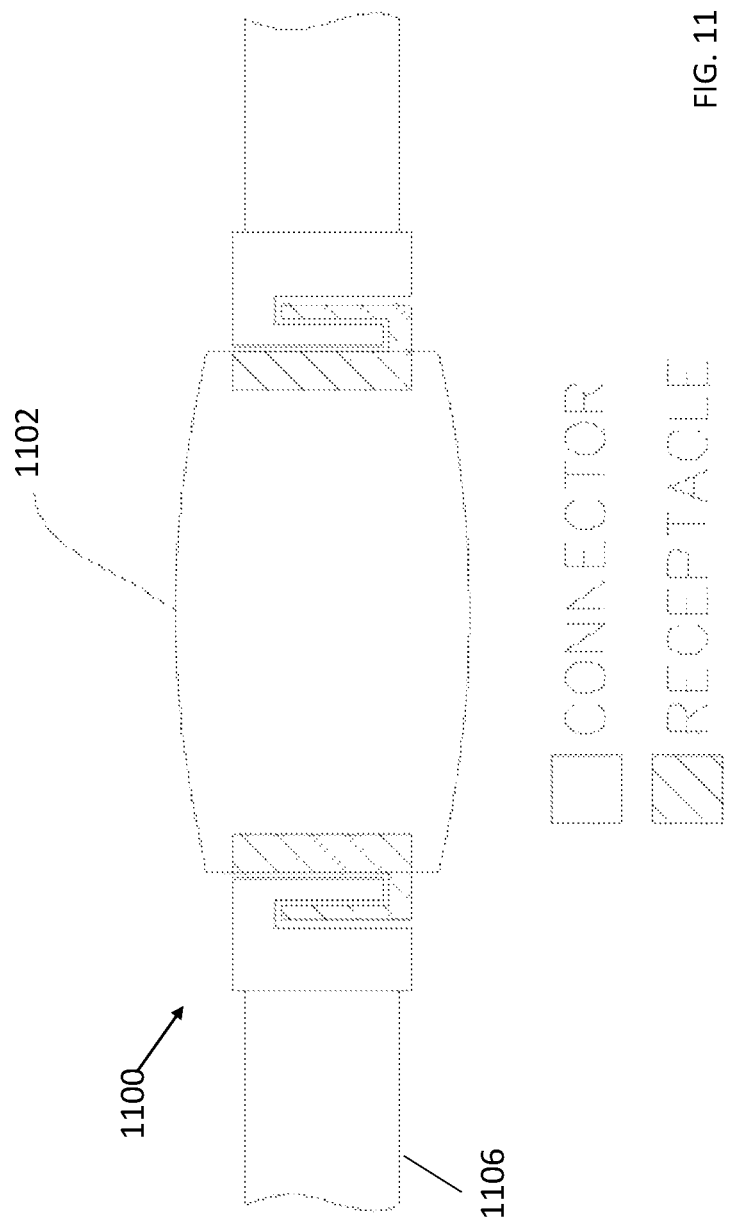
FIG. 11 is a front perspective view of a respiratory effort connector system coupled with an inert belt coupled with an HSAT device.

FIG. 11 is a front perspective view of a respiratory effort connector system 1100 coupled with an inert belt 1106 coupled with an HSAT device 1102. In the example embodiment the belt 1106 is inert and contains no sensing elements. The belt 1106 serves solely as a support belt for the device 1102. In some embodiments the belt 1106 is reusable, while in other embodiments the belt 1106 is disposable.

Figure 12:
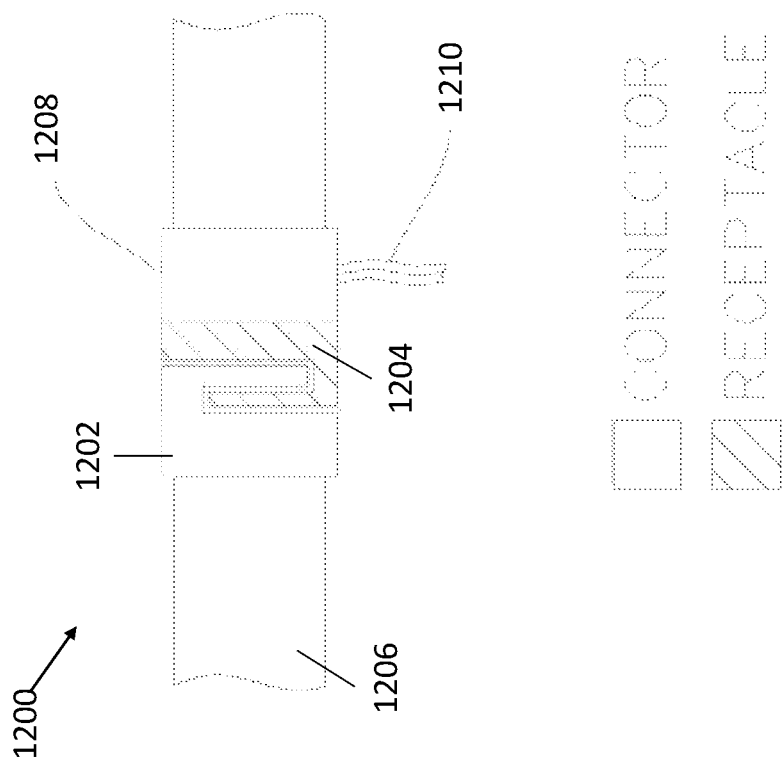
FIG. 12 is a front perspective view of a respiratory effort connector system coupled with a belt containing integrated circuitry.

FIG. 12 is a front perspective view of a respiratory effort connector system 1200 coupled with a belt 1206 containing integrated circuitry. As shown in the example embodiment, one end of the belt 1206 is coupled with or includes a connector 1202. Another end of the belt 1206 is coupled with or includes a receptacle 1204. Receptacle 1204 comprises a housing 1208 that can also include internally stored sensor driver circuitry. A lead wire 1210 can exit through a hole in housing 1208 and can be appropriately connected to a sleep amplifier. In some embodiments the sensor circuitry can be in a housing of connector 1202. This configuration can improve on currently existing products that include a separate sensor driver device and additional lead wire connection.

Figure 13:
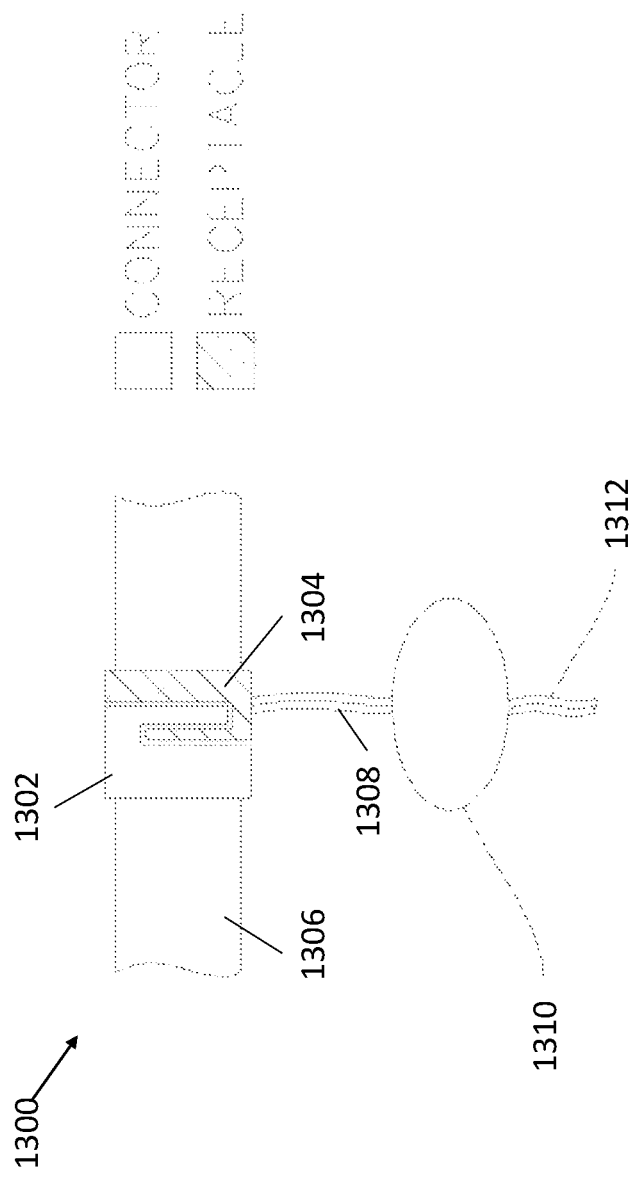
FIG. 13 is a front perspective view of a respiratory effort connector system coupled with a sensor driver.

FIG. 13 is a front perspective view of a respiratory effort connector system 1300 coupled with a sensor driver 1310. Here, belt 1306, connector 1302, and receptacle 1304 are configured similarly to the embodiment shown and described with respect to FIG. 12. However, in FIG. 13, wire 1308 connects to sensor driver 1310 externally. This configuration can be a captive wireset or a separate connector input. A wire 1312 can be connected to sensor driver 1310 at one end and to a sleep amplifier (not shown) at the other end.

FIG. 14 is a front perspective view of an inert respiratory effort connector system 1400. As shown in the example embodiment, a belt 1406 can have no electrical connection and the connector system with connector 1402 and receptacle 1404 can be employed in place of a traditional buckle system.

The foregoing is provided for purposes of illustrating, explaining, and describing embodiments of this disclosure. Modifications and adaptations to these embodiments will be apparent to those skilled in the art and may be made without departing from the scope or spirit of this disclosure.

Although the subject matter has been described in terms of exemplary embodiments, it is not limited thereto. Rather, the appended claims should be construed broadly, to include other variants and embodiments, which may be made by those skilled in the art.

We claim:

1. A respiratory effort belt connection system, comprising:
   a receptacle having a receptacle housing,
      wherein the receptacle housing comprises a receptacle opening formed by a longitudinal cavity in a top portion of the receptacle housing,
      wherein the receptacle housing comprises a guide notch formed by a vertical cavity in a side of a top the receptacle housing,
      wherein the receptacle housing comprises a locking recess formed by a rectangular cavity in an upper side portion of the receptacle housing, and wherein the longitudinal cavity, vertical cavity, and rectangular cavity are fluidly coupled, and
      wherein the receptacle housing comprises a locking lug located above the locking recess formed by a portion of the side of the top of the receptacle housing without the guide notch;
   a connector,
      wherein the connector comprises a barrel having an end configured to be inserted into the receptacle opening,
      wherein the connector comprises a locking bar coupled to the barrel and configured to be aligned and inserted into the guide notch, rotated into the locking recess, and retain by the locking lug of the receptacle,
      wherein the connector comprises a grip, and
      a connector neck, wherein the connector neck is coupled to the grip and the barrel;
   a belt; and
   a device, wherein the belt is coupled to the grip of the connector and the device is coupled to the receptacle housing of the receptacle, or vice versa.

2. The respiratory effort belt of claim 1, wherein the grip is coupled to an end of the locking bar opposite that of the barrel, and wherein the grip has a shape of a rectangular prism with rounded corners.

3. The respiratory effort belt of claim 1, wherein the connector neck extends from a top section of the grip to a top portion of the barrel, and wherein the connector neck has an internal cavity to allow an electrical conductor to pass between the grip and the barrel.

4. The respiratory effort belt of claim 1, wherein the respiratory effort belt further comprises an additional connector coupled to the belt and an additional receptacle housing of an additional receptacle coupled to the sleep monitor device.

5. The respiratory effort belt of claim 1, wherein the receptacle housing comprises an additional locking recess and an additional locking lug, and the connector comprises an additional locking bar coupled to the barrel.

6. The respiratory effort belt of claim 1, wherein the locking recess adjacent to the guide notch is configured to be further from the patient than the guide notch when the belt is fully fastened.

7. The respiratory effort belt of claim 1, wherein the barrel of the connector has a tapered cylindrical shape that substantially matches a shape of a central tapered cylindrical cavity formed in the receptacle housing below the receptacle opening.

8. The respiratory effort belt of claim 1, wherein the locking bar is located about midway along a length of the barrel and perpendicular to a central axis of the barrel.

9. The respiratory effort belt of claim 1, wherein the width of the locking recess is about 60 degrees.

10. The respiratory effort belt of claim 1, wherein a width of the guide notch is about mm.

11. The respiratory effort belt of claim 1, wherein the aligned and inserted locking bar is configured to be rotated through an angle of about 60 degrees from the vertical guide notch into the locking recess.

12. The respiratory effort belt of claim 1, wherein the device analyses breathing parameters of a user.

13. The respiratory effort belt of claim 1, wherein a connector electrical contact is located within a touchproof recess formed by a cavity in a bottom of the barrel.

14. The respiratory effort belt of claim 13, wherein a receptacle electrical contact is located within a touchproof connector well formed by a cavity in a base of the receptacle housing.

15. The respiratory effort belt of claim 14, wherein the connector electrical contact and the receptacle electrical contact are rotary type electrical connectors.

16. A method for securing a respiratory effort belt to a patient, the method comprising:
    inserting an end of a barrel of a connector into a receptacle opening formed by a longitudinal cavity in a top portion of a receptacle housing of a receptacle;
    rotating the barrel of the connector with respect to the receptacle housing until a bottom of a locking bar coupled to the barrel is aligned with a vertical guide notch formed by a vertical cavity in a side of the top portion of the receptacle housing; and
    inserting the aligned locking bar into the vertical guide notch until the locking bar is fully seated within the vertical guide notch and adjacent to a locking recess formed by a cavity within an upper portion of the receptacle housing; and
    rotating the barrel of the connector with respect to the receptacle housing until the locking bar is substantially located within the locking recess, wherein the locking bar is retained by a locking lug located above the locking recess formed by a portion of the side of the top of the receptacle housing without the guide notch.

17. The method of claim 16, further comprising:
    rotating the barrel of the connector with respect to the receptacle housing until the locking bar is outside of the locking recess and aligned and fully seated within the vertical guide notch, wherein the locking bar is no longer retained by the locking lug; and
    removing the aligned locking bar until the locking bar is no longer within the guide notch and an end of the barrel clears the receptacle opening formed in a top of the receptacle housing of the receptable.

18. The method of claim 16, wherein the barrel of the connector has a tapered cylindrical shape that substantially matches a shape of a central tapered cylindrical cavity formed in the receptacle housing below the receptacle opening.

19. The method of claim 16, wherein the locking bar is located about midway along a length of the barrel and perpendicular to a central axis of the barrel.

20. The method of claim 16, further comprising positioning the receptacle so that the locking recess adjacent to the vertical guide notch is further from the patient than the guide notch when the belt is fully fastened.

* * * * *